United States Patent [19]
Wong

[11] Patent Number: 5,340,986
[45] Date of Patent: * Aug. 23, 1994

[54] DIFFUSION-TYPE GAS SAMPLE CHAMBER

[75] Inventor: Jacob Y. Wong, Santa Barbara, Calif.

[73] Assignee: Gaztech International Corporation, Goleta, Calif.

[*] Notice: The portion of the term of this patent subsequent to Nov. 17, 2009 has been disclaimed.

[21] Appl. No.: 915,003

[22] Filed: Jul. 16, 1992

Related U.S. Application Data

[63] Continuation-in-part of Ser. No. 793,990, Nov. 18, 1991, Pat. No. 5,163,332.

[51] Int. Cl.$^5$ .............................. G01N 21/61
[52] U.S. Cl. ................. 250/343; 250/338.5; 356/437
[58] Field of Search ........... 250/343, 345, 373, 338.5; 356/437, 440

[56] References Cited

U.S. PATENT DOCUMENTS

| | | | |
|---|---|---|---|
| 4,749,276 | 6/1988 | Bragg et al. | 250/343 |
| 5,125,742 | 6/1992 | Wilks, Jr. | 356/440 |
| 5,163,332 | 11/1992 | Wong | 356/437 |

FOREIGN PATENT DOCUMENTS 257347 12/1985 Japan .................................. 250/343

*Primary Examiner*—Carolyn E. Fields
*Attorney, Agent, or Firm*—Daniel C. McKown

[57] ABSTRACT

The improved sample chamber includes an elongated hollow tube closed at one end and having specularly-reflective inwardly facing surfaces. A source of radiation and a detector of radiation are mounted side by side in the open end of the hollow tube, both facing the closed end. A plurality of filtering apertures are formed in the tube, and each aperture is covered by a sheet of a semipermeable membrane that serves to prevent airborne particles larger than a predetermined size from entering the chamber while not interfering with the free diffusion of the gas to be measured into and out of the chamber. The use of an elongated hollow tube that is closed at one end results in no loss in the efficiency with which the radiation is conducted from the source to the detector while decreasing the external length of the chamber by 50 percent.

4 Claims, 1 Drawing Sheet

DIFFUSION-TYPE GAS SAMPLE CHAMBER

RELATED APPLICATIONS

The present application is a continuation-in-part of U.S. applications Ser. No. 07/793,990 for GAS SAMPLE CHAMBER filed Nov. 18, 1991, now U.S. Pat. No. 5,163,332. The disclosure of that application is incorporated herein by reference to avoid unnecessary repetition of background material.

BACKGROUND OF THE INVENTION

1. Field of the Invention

The present invention is in the field of gas analysis, and specifically relates to apparatus using a nondispersive infrared gas analysis technique to determine the concentration of a particular type of gas present in a sample chamber by sensing the absorption of infrared radiation passing through the gas.

2. The Prior Art

A comparatively new development in the field of nondispersive infrared gas analyzers has been the diffusion-type gas sample chamber. In a diffusion-type gas sample chamber, the gas to be measured enters and leaves the chamber by diffusion.

One example of a diffusion-type gas sample chamber is described in the parent application. In that invention, the sample chamber has the form of a tube composed of a gastight material, having apertures covered by semipermeable membranes through which the gas to be measured enters and leaves the sample chamber by diffusion. This same approach is used in the present invention, with some important modifications.

Another example of a diffusion-type gas sample chamber is described in U.S. Pat. No. 4,709,150 to Burough et al. In their invention, the body of the sample chamber is composed of a porous material through which the gas to be measured passes by diffusion. Burough et al. do not teach or suggest using the walls of the porous tube as reflective radiation-guiding elements.

An example of a non-diffusion-type gas sample chamber is shown in Japanese Patent Publication No. 59-173734(A) of Miyazaki. In that analyzer, the sample cells have the form of helical tubes. The gas to be measured must be pressurized to force it to flow through the sample tube.

Another example of a non-diffusion-type of gas sample chamber is shown in Japanese Publication No. 63-298031 by Fujimura, in which air is rammed into the sample chamber by motion of the sample chamber through the air.

In the present application, the inventor will describe an improvement on the sample chamber described in the parent application to make it more compact while maintaining its radiation-handling efficiency.

SUMMARY OF THE INVENTION

In the gas sample chamber of the parent application, the gas sample chamber includes a tube that is open at both ends; the source of radiation is centered at one end, and the detector of radiation is centered at the opposite end. In contrast, in accordance with the present invention the gas sample chamber includes a tube that is closed at one end, and both the source of radiation and the detector are mounted at off-center positions in the open end.

When the present inventor started his experiments leading up to the present invention, it was not known what the effect would be of closing one end of the tube. Nor was it known what the effect would be of mounting the detector and the source of radiation at off-center positions.

After a series of experiments, the present inventor was able to show that when the end of the tube is closed, the path length of the radiation is effectively doubled as compared with a tube of the same length but open at both ends. The experiments also proved that little loss results from mounting the source of radiation and the detector at off-center positions.

Thus, compared with a tube that is open at both ends, the sample chamber of the present invention is twice as sensitive. Alternatively, the tube of the present invention can achieve the same sensitivity with a sample chamber that is only half as long.

The novel features which are believed to be characteristic of the invention, both as to organization and method of operation, together with further objects and advantages thereof, will be better understood from the following description considered in connection with the accompanying drawing in which a preferred embodiment of the invention is illustrated by way of example. It is to be expressly understood, however, that the drawing is for the purpose of illustration and description only and is not intended as a definition of the limits of the invention.

DETAILED DESCRIPTION OF THE PREFERRED EMBODIMENT

Figure 1:
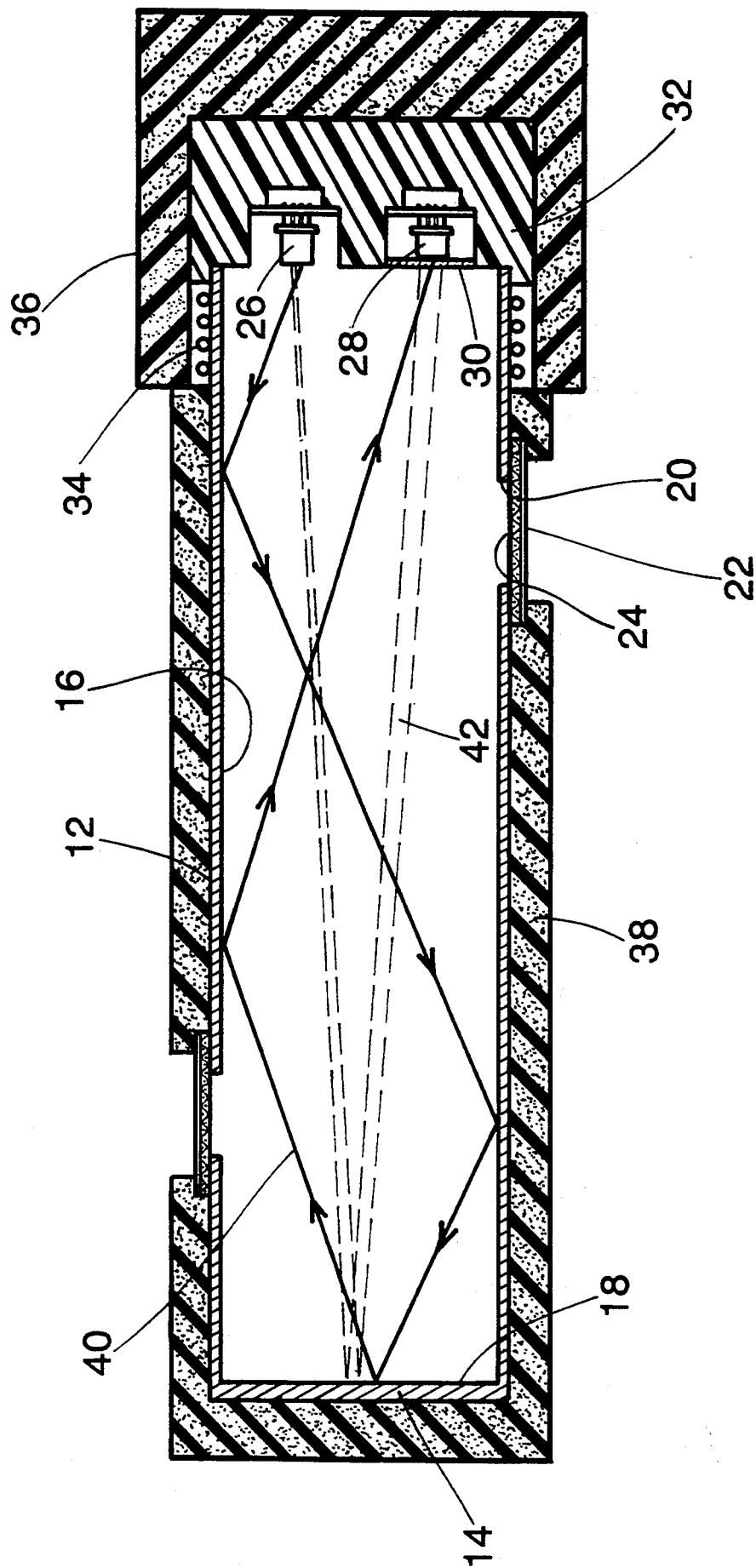
FIG. 1 is a diagram showing a side elevational cross-sectional view of the improved diffusion-type gas sample chamber of the present invention.

In a preferred embodiment, the gas sample chamber of the present invention includes a tube 12 having a closed end 14 and having an open end. In the preferred embodiment, the tube 12 is composed of a metal, and has a square cross section. In other embodiments, the cross section is circular.

The surface of the inner wall 16 of the tube 12 and the inwardly-facing surface 18 of the closed end 14 are specularly-reflective.

In accordance with the present invention, the metal tube 12 is gastight and therefore filtering apertures, of which the filtering aperture 20 is typical, are provided at spaced locations along the tube 12 to permit molecules of the gas to be detected to enter and to leave the space within the tube. Each of the filtering apertures 20 is covered by a sheet of a semipermeable membrane 22.

In the preferred embodiment, the gas to be detected is carbon dioxide, and the semipermeable membrane is composed of silicone rubber and is approximately 25 to 50 microns thick. Because of its fragility, in the preferred embodiment the semipermeable membrane 22 is supported by a mesh 24 that spans the aperture 20. At this point in time, the exact number, location, and disposition of the filtering apertures does not appear to be crucial, although some as-yet-undiscovered arrangement may be optimal.

The open end of the tube 12 is closed by a cap 32 in which are mounted a source 26 of radiation, a detector 28, and a narrow passband filter 30. The passband of the filter 30 is located at a wavelength at which the gas to be detected strongly absorbs radiation and at which any other gases that might be present do not absorb. The source 26 emits radiation in the same absorption band. The concentration within the sample chamber of the gas to be detected is related to the extent to which the radiation is absorbed. The plastic cap 32 serves to mount the source 26 and the detector 28 and the filter 30 in the open end of the tube 12 with the source 26 and the detector 28 facing the surface 18.

Some of the radiation emitted by the source 26 is simply reflected from the surface 18 directly back to the detector 28. In FIG. 1, this component of the radiation is defined by the bundle 42 of rays. It is clear from FIG. 1 that if this were the only mode of propagation, then only an extremely small fraction of the emitted radiation would reach the detector 28. The solid angle of the detector at a distance equal to twice the length of the tube 12 is extremely small.

An important advantage of using the tube 12 is that it permits other modes of propagation from the source to the detector to occur. The amount of radiation contributed by the various modes of transmission is additive since the successive modes are characterized by progressively steeper rays. Compared with a simple plane mirror such as the surface 18, the addition of the tube 12 greatly increases the amount of radiation that reaches the detector 28. One might consider the bundle 42 of rays to represent the simplest or fundamental mode, and the ray 40 to represent one of the higher order modes of propagation.

In addition to making it possible to utilize the higher order modes of propagation, the addition of the tube 12 produces a secondary benefit, namely, that the radiation travels a greater distance through the space within the tube as the order of the mode of propagation increases. That is, for the higher modes, the rays are steeper resulting in a greater distance of travel back and forth across the tube, notwithstanding that the distance traveled in the longitudinal direction remains constant and simply equals twice the length of the tube.

The purpose of the semipermeable membrane 22 is to prevent airborne particles larger than a predetermined size from entering the space within the tube 12, while at the same time not interfering appreciably with the free diffusion of the gas to be detected into and out of the space within the tube 12. The unwanted particles include minute droplets of moisture or oil and also include fine particulate matter such as particles of dust or smoke. If these unwanted airborne particles were to enter the space within the tube 12, they would deposit themselves onto the specularly reflective surfaces thereby reducing the reflectivity and destroying its specular nature. The unwanted particles would also deposit onto the source 26 and onto the narrow passband filter 30 reducing the transmission of radiation and possibly causing chemical changes to take place. All of these problems are eliminated through the use of the semipermeable membrane which, in the preferred embodiment prevents airborne particles larger than 0.3 microns from entering the space within the tube 12.

Unfortunately, the semipermeable membrane cannot prevent molecules of water from diffusing into the space within the tube 12, and if the components within the space are at a sufficiently low temperature, there is a possibility that the water vapor may condense onto the cold surfaces. To prevent that from happening, heater wires 34 are employed in the preferred embodiment to generate heat by ohmic heating when an electric current is passed through them. To minimize the escape of this heat, the metal tube 12, which is an excellent conductor, is provided with an insulative sheath 38. Likewise, the cap 32 is provided with an insulative casing 36. Because of the proximity of the wires 34 to the source 26 and the filter 30, these components are also protected from moisture condensing upon them.

Thus, there has been described an improved diffusion-type gas sample chamber which differs from previous sample chambers in that both the radiation source and the detector are mounted side by side at the same end of the tubular sample chamber. Compared to previously known sample chambers, the chamber of the present invention efficiently collects and conducts the radiation to the detector while using a tube that is only half as long.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. An improved diffusion-type gas sample chamber for transmitting radiation through gases present in the chamber by ambient pressure diffusion, comprising in combination
    a) an elongated hollow tube having an inner wall and having a closed end and an open end, composed of a gastight material and having a specularly-reflective surface on the inner wall and on the inwardly-facing side of the closed end;
    b) said tube including a plurality of filtering apertures arrayed along said tube for improving the diffusion into and out of the space within said tube;
    c) a sheet of a semipermeable membrane covering each of said plurality of filtering apertures, said semipermeable membrane permitting gases to diffuse through it under ambient pressure into and out of the space within said tube and preventing airborne particles larger than a predetermined size from entering said space;
    d) a source of radiation;
    e) a detector of radiation; and,
    f) means for mounting both said source of radiation and said detector of radiation proximate said open end and facing said closed end, whereby some of the radiation emitted in various directions from said source of radiation is conducted by at least one reflection from the specularly-reflective surface on the inner wall to the specularly-reflective surface on the inwardly-facing side of the closed end and from the latter by at least one reflection from the specularly-reflective surface on the inner wall to said detector of radiation.

2. The improved diffusion-type gas sample chamber of claim 1 further comprising heater means adjacent the open end of said tube for supplying heat to said tube to prevent condensation on said source of radiation, on said detector of radiation and on said specularly-reflective surface.

3. The improved diffusion-type gas sample chamber of claim 1 wherein said predetermined size is 0.3 microns.

4. The improved diffusion-type gas sample chamber of claim 1 wherein said detector of radiation includes a narrow passband filter.

* * * * *